United States Patent [19]

Fellman

[11] Patent Number: 5,326,841
[45] Date of Patent: Jul. 5, 1994

[54] GERMICIDAL BARRIERS

[75] Inventor: Jack H. Fellman, Portland, Oreg.

[73] Assignee: Epitope, Inc., Beaverton, Oreg.

[21] Appl. No.: 370,683

[22] Filed: Jun. 23, 1989

Related U.S. Application Data

[63] Continuation-in-part of Ser. No. 301,099, Jan. 25, 1989, abandoned.

[51] Int. Cl.$^5$ .................. C08F 20/04; C08F 20/52; C08F 20/70; A61K 31/74
[52] U.S. Cl. .................. 526/292.3; 526/292.2; 526/292.7; 526/310; 424/78.37
[58] Field of Search .............. 526/292.3, 292.2, 292.7, 526/310; 424/78.37

[56] References Cited

U.S. PATENT DOCUMENTS

| | | | |
|---|---|---|---|
| 3,011,918 | 12/1961 | Silvernail et al. | 526/310 |
| 3,028,301 | 4/1962 | Winicov | 514/642 |
| 3,279,981 | 10/1966 | Geiger et al. | |
| 3,496,109 | 2/1970 | Walker et al. | |
| 3,539,684 | 11/1970 | Hoover et al. | 526/310 |
| 3,678,098 | 7/1972 | Lewis et al. | 526/292.2 |
| 3,766,156 | 10/1973 | Kine et al. | |
| 3,825,511 | 7/1974 | Markhart et al. | |
| 3,874,870 | 4/1975 | Green et al. | |
| 3,898,336 | 8/1975 | Rembaum et al. | |
| 3,901,857 | 8/1975 | Sackman et al. | 526/292.2 |
| 3,923,973 | 12/1975 | Green et al. | |
| 3,929,990 | 12/1975 | Green et al. | |
| 4,001,432 | 1/1977 | Green et al. | |
| 4,005,193 | 1/1977 | Green et al. | |
| 4,016,128 | 4/1977 | Serlin et al. | |
| 4,025,617 | 5/1977 | Green et al. | |
| 4,026,945 | 5/1977 | Green et al. | |
| 4,027,020 | 5/1977 | Green et al. | |
| 4,035,480 | 7/1977 | Green et al. | |
| 4,036,959 | 7/1977 | Green et al. | |
| 4,046,725 | 9/1977 | Pusineri | 523/112 |
| 4,055,712 | 10/1977 | Green et al. | |
| 4,060,678 | 11/1977 | Steckler | 526/310 |
| 4,075,136 | 2/1978 | Schaper | |
| 4,075,183 | 2/1978 | Kawakami et al. | 526/292.2 |
| 4,089,977 | 5/1978 | Green et al. | |
| 4,091,113 | 5/1978 | Green et al. | |
| 4,111,679 | 9/1978 | Shair et al. | |
| 4,111,922 | 9/1978 | Beede et al. | 526/292.2 |
| 4,158,726 | 6/1979 | Kamada et al. | 526/292.2 |
| 4,182,849 | 1/1980 | Ezzell | |
| 4,218,554 | 8/1980 | Foley, Jr. | 526/292.2 |
| 4,247,476 | 1/1981 | Haase et al. | |
| 4,452,957 | 6/1984 | Neigel | 256/310 |
| 4,581,058 | 4/1986 | Fenyes et al. | |
| 4,606,916 | 8/1986 | Hofinger et al. | 424/70 |
| 4,617,362 | 10/1986 | Becker et al. | 526/292.2 |
| 4,621,120 | 11/1986 | Hollister | 424/78.18 |

FOREIGN PATENT DOCUMENTS

| | | | |
|---|---|---|---|
| 0141628 | 5/1985 | European Pat. Off. | |
| 0144975 | 6/1985 | European Pat. Off. | |
| 0335624 | 10/1989 | European Pat. Off. | 526/292.2 |
| 45-37032 | 11/1970 | Japan | 526/310 |
| 48-30479 | 9/1973 | Japan | 526/292.2 |
| 0117304 | 7/1984 | Japan | 526/310 |
| 60-26346 | 2/1985 | Japan | 526/310 |

*Primary Examiner*—Paul R. Michl
*Assistant Examiner*—Peter Szekely
*Attorney, Agent, or Firm*—Wegner, Cantor, Mueller & Player

[57] ABSTRACT

Disclosed is an elastomeric article comprising the cross-linked, polymerized product of (i) a quaternary ammonium compound having the formula $N^+R_4X^-$ wherein at least one of the R groups is unsaturated alkyl and the remaining R groups alkyl or aryl and X is halogen or a small anion with (ii) a free-radical co-polymerizable compound.

29 Claims, No Drawings

GERMICIDAL BARRIERS

This application is a continuation-in-part of U.S. patent application Ser. No. 301,099, filed Jan. 25, 1989, now abandoned.

The present invention relates to polymers having quaternary ammonium functionality. In particular, it relates to such polymers that are complexed with useful pharmaceutical agents.

Polymers having quaternary ammonium frunctionality are well known. Such polymers have been complexed with iodine and used as germicidal agents in, e.g., detergents, etc.

The present invention is an elastomeric article comprising the cross-linked, polymerized product of (i) a quaternary ammonium compound having the formula N+R$_4$X− wherein at least one of the R groups is unsaturated alkyl and the remaining R groups alkyl or aryl and X is halogen or a small anion with (ii) a free-radical co-polymerizable compound. The present invention is also a polymer having repeating units of the formula

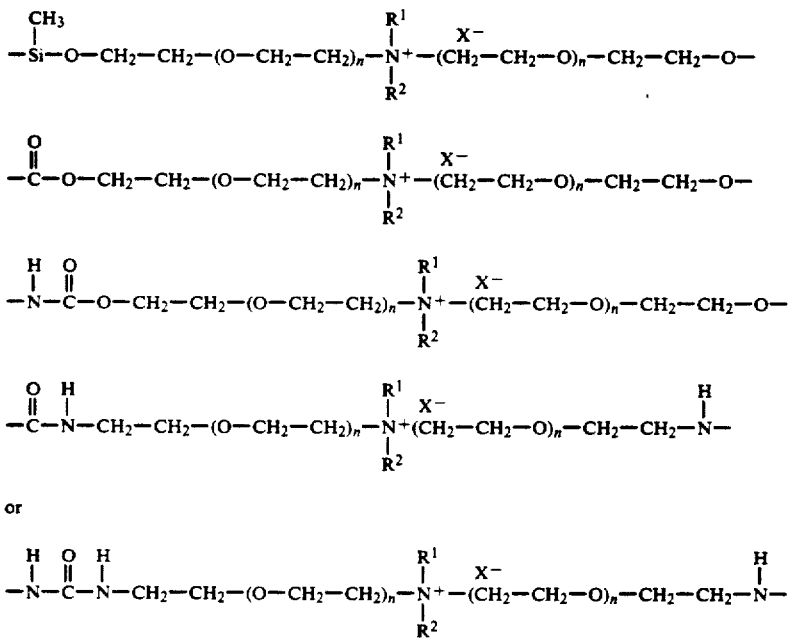

wherein R$^1$ and R$^2$ are independently alkyl or aryl and n is an integer from 0–50. The present invention is useful in making elastomeric articles, such as condoms and surgical gloves.

In the above formula N+R$_4$X− at least one of the R groups is an unsaturated alkyl, e.g., a short chain (C$_1$–C$_4$) alkenyl such as vinyl or allyl, or a long chain (C$_5$–C$_{20}$) mono- or poly-unsaturated alkyl group. The remaining R groups are C$_1$–C$_{20}$ alkyl groups such as methyl, ethyl, propyl, butyl, stearyl, decyl, or dodecyl, unsubstituted and lower alkyl-substituted aryl groups including aromatically bonded aryl groups such as phenyl or tolyl, and aliphatically bonded aryl groups such as benzyl, or nitrogen heterocyclic groups such as pyridyl. The variable X− is halogen, preferably chlorine, bromine, or iodine, or a suitably small anion such as acetate, sulfate, or citrate. Examples of these quaternary ammonium compounds include N-oleyl-N-trimethyl ammonium chloride, N-oleyl-N-trimethyl ammonium iodide, and N-oleyl pyridinium chloride.

The co-polymerizable compound that is reacted with the compound of the formula N+R$_4$X− to make the elastomeric article of the present invention is a polymer such as natural latex, acrylamide polymers, polymers of methyl, ethyl, propyl, or butyl acryl esters, vinyl chloride polymers, or vinyl acetate polymers. The co-polymerizable compound can also be one or more polymerizable monomers such as methyl vinylsiloxanes and dimethylsiloxanes. When using latex as the copolymerizable compound, in the compound of the formula N+R$_4$X− only one of the R groups is unsaturated, and the unsaturated group is a long chain, preferably C$_{16}$–C$_{20}$, mono- or poly-unsaturated alkyl group, and the remaining R groups are C$_{1-4}$ alkyl or aryl. In acrylamide and vinyl copolymer systems, preferably 2 or 3 of the R groups are unsaturated groups, and the unsaturated groups are short chain alkenyls such as vinyl and allyl.

The compound of the formula N+R$_4$X− is reacted with the co-polymerizable compound by known free-radical polymerization techniques. Such techniques include heating to a temperature between about 100° and 300° C., optionally in the presence of suitable known adjuvants in polymerization and cross-linking techniques, including free-radical initiators such as ammonium persulfate, potassium persulfate, sodium persulfate, or hydrogen peroxide, cross-linking agents such as N-N-methylene bis-acrylamide, and accelerators such as tetramethyl ethylene diammonium bases, as well as ultraviolet light-initiated polymerization. Preferably, the amount of the compound of the formula N+R$_4$X− used in the reaction varies between about 0.001 and 10%, more preferably between about 0.1 and 1.5%, most preferably between about 0.5 and 1.5%, by weight of the reaction mixture, i.e., the total weight of the compound of the formula N+R$_4$X− plus the copolymerizable compound. Depending on the reactants and reaction conditions, cross-linking is effected either during or following the polymerization reaction to form an elastomer. If cross-linking occurs during polymerization, the reaction mixture is preferably formed into the shape of the desired product before polymerization.

The polymer of the present invention is made by reacting a quaternary ammonium compound of the formula

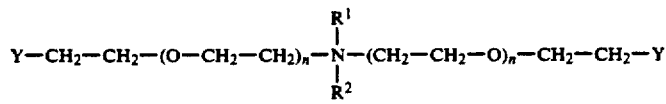

wherein —Y is —OH or —NH$_2$, R$^1$ and R$^2$ are independently alkyl or aryl, and n is an integer from 0–50 with a condensation co-polymerizable compound to form a polyurethane, polyester, or polydimethylsiloxane when —Y is —OH, or polyamide or polyurea when —Y is —NH$_2$. R$^1$ and R$^2$ are C$_1$-C$_{20}$ alkyl groups such as methyl, ethyl, propyl, butyl, stearyl, decyl, or dodecyl, aryl groups such as phenyl, benzyl, or tolyl, or nitrogen heterocyclic groups such as pyridyl. Preferably n is an integer between about 1 and 50, more preferably between about 10 and 30.

The polydimethylsiloxane thereby produced has repeating units of the formula

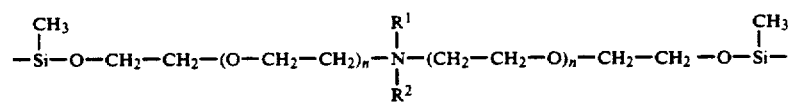

wherein R$^1$, R$^2$ and n are as defined above. The polydimethylsiloxane is made by including the quaternary ammonium alcohol in well known polydimethylsiloxane reactions, e.g., by reacting a silanol or hydrolyzable silane with the quaternary ammonium compound. The amount of quaternary ammonium compound used varies between about 0.001 and 10%, preferably between about 0.5 and 1.5%, by weight of the reaction mixture, i.e., the total weight of the quaternary ammonium compound and the co-polymerizable compound.

The polyester thereby produced has repeating units of the formula

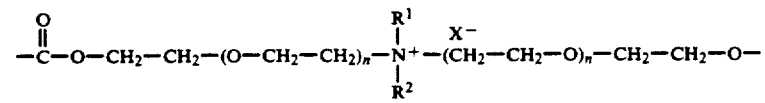

wherein R$^1$, R$^2$, and n are as defined above. The polyester is made including the quaternary ammonium dialcohol in well known polyester condensation reactions, e.g., by reacting the quaternary ammonium dialcohol with a carboxylic acid and a glycol. The amount of quaternary ammonium dialcohol used varies between about 0.001 and 10%, preferably between about 0.5 and 1.5%, by weight of the reaction mixture, i.e., the total weight of the quaternary ammonium compound and the copolymerizable compound.

The polyurethane of the present invention has repeating units of the formula

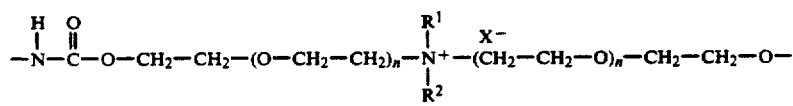

wherein R$^1$, R$^2$, and n are as defined above. The polyurethane is made by including the quaternary ammonium dialcohol in well known polyurethane formation reactions, e.g., by reacting the dialcohol with a diisocyanate and a glycol. The amount of quaternary ammonium dialcohol used varies between about 0.001 and 10%, preferably between about 0.5 and 1.5%, by weight of the reaction mixture, i.e., the total weight of the quaternary ammonium compound and the copolymerizable compound.

The polyamide of the present has repeating units of the formula

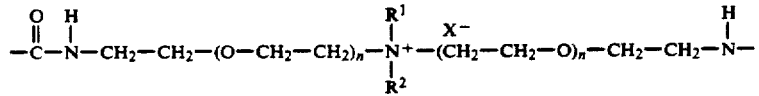

wherein R$^1$, R$^2$, and n are as defined above. The polyamide is made by including the quaternary ammonium diamine in well known polyamide formation reactions, e.g., by reacting the diamine with an acid chloride. The amount of quaternary ammonium diamine used varies between about 0.001 and 10%, preferably between about 0.5 and 1.5%, by weight of the reaction mixture, i.e., the total weight of the quaternary ammonium compound and the co-polymerizable compound.

The polyurea of the present invention has repeating units of the formula

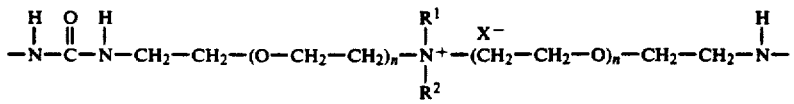

wherein $R^1$, $R^2$, and n are as defined above. The polyurea is made by including the quaternary ammonium diamine in well known polyamine formation reactions, e.g., by reacting the diamine with a diisocyanate. The amount of quaternary ammonium diamine used varies between about 0.001 and 10%, preferably between about o.5 and 1.5%, by weight of the reaction mixture, i.e., the total weight of the quaternary ammonium compound and the co-polymerizable compound.

To more fully describe the present invention, the following non-limiting examples are provided. In the examples, all parts and percentages are by weight unless otherwise indicated.

EXAMPLE 1

A latex/quaternary ammonium polymer is made and formed into a condom. To 100 ml of natural Malaysian latex (polyisoprene; about 60% solids in an ammoniacal water-based emulsion) is added 1.0 g of N,N,N-trimethyl-N-oleylammonium iodide dissolved in 30 ml water. The mixture is stirred to form a homogeneous emulsion. Condom forms are dipped into the emulsion and heated at 110° C. until cured. The condoms are submerged for about 5 seconds in iodine dissolved in ethanol. The iodine complexes with the quaternary ammonium moiety in the polymer to form a germicidal barrier.

EXAMPLE 2

An acrylamide/quaternary ammonium polymer is made and formed into a coating for a surgical face mask. A mixture of 10% acrylamide, 10% bis-acrylamide, 1% of 1% N,N-dimethyl-N,N-dioleyl ammonium chloride, and water is prepared, with percentages based on the total weight of the mixture. Ammonium persulfate (or other alkali metal, such as potassium, salt) at 1% is added to the mixture to initiate polymerization, which is allowed to proceed until a gel is formed. The gel is applied to a surgical face mask and allowed to dry. The mask is then treated with iodine as in EXAMPLE 1.

EXAMPLE 3

A polyester/quaternary ammonium polymer is formed and used as a coating for a surgical face mask. In a reactor are charged 10 millimoles diethylfumarate, 0.02 millimole sodium metal, 9 millimoles ethylene glycol, and 1 millimole of N-methyl-N-stearyl-N-bis(-polyethylene glycol)$_{n=24}$ iodide under a nitrogen atmosphere. The mixture is heated at 45°–50° C. for one hour, then the temperature is gradually increased to about 110° C. and maintained at that temperature for about 72 hours, after which the pressure is reduced from an initial pressure of 1 atm of nitrogen to about 10 mm mercury. The resin obtained is applied to packaging material made of a synthetic fabric by spraying a solution of the resin in alcohol onto the material, and then treated with iodine as in EXAMPLE 1 to form a self-sterilizing wrapping.

EXAMPLE 4

A polyurethane/quaternary ammonium polymer is formed. To a vessel fitted with a dropping funnel, stirrer, thermometer, and condenser is added lo millimoles of toluene-2,4-diisocyanate, 9 millimoles of ethylene glycol, and one millimole of N-methyl-N-stearyl-N-bis(-polyethylene glycol)$_{n=24}$ iodide in 20 ml ethylacetate, which is stirred under a nitrogen atmosphere. The vessel is heated at 80° C. for 24 hours, one drop of triethyl amine is added, and the heating is continued for another hour. The resulting material is rotary evaporated, and then complexed with iodine as in EXAMPLE 1. Alternatively, after the material is rotary evaporated, it is applied to packaging material and treated with iodine as in Example 3.

EXAMPLE 5

A silicon/quaternary ammonium polymer is made and formed into a condom. Monomer blends are prepared containing N-methyl-N-stearyl-N-bis(polyethylene glycol)$_{n=24}$ iodide at various amounts (0.01 part, 0.1 part, 1.0 part, and 10 parts) is mixed with 10 parts of a mixture containing 65 parts vinyl methyl siloxane and 35 parts of 80% 1,333 tetra-methyl, disiloxane. To each blend 6 parts per million (ppm) chloroplatinate is added as a catalyst. Phallic forms are dipped into the mixture, and then heated to about 100° C. for about 30 minutes. The resulting condoms are treated by submerging both sides in a solution of 1% $KI_3$ in water.

What is claimed is:

1. An elastomeric article comprising the cross-linked, polymerized product of (i) a quaternary ammonium compound having the formula $N^+R_4X^-$ wherein at least one of the R groups is a hydrophobic unsaturated alkyl and the remaining R groups are hydrophobic alkyl or aryl and X is halogen or a small anion with (ii) a free-radical co-polymerizable compound, wherein the product is complexed with iodine.

2. The article of claim 1 wherein the quaternary ammonium compound is N-trimethyl-N-oleylammonium iodide.

3. The article of claim 1 wherein the co-polymerizable compound is latex rubber.

4. The article of claim 1 wherein the copolymerizable compound is a mixture of methyl vinylcyclosiloxane and dimethylsiloxane.

5. The article of claim 1 wherein the co-polymerizable compound is an acrylamide.

6. The article of claim 1 complexed with iodine.

7. A process for making an elastomeric article comprising the steps of:
   (a) polymerizing (i) a quaternary ammonium compound having the formula $N^+R_4X^-$ wherein at least one of the R groups is a hydrophobic unsaturated alkyl and the remaining R groups hydrophobic alkyl or aryl and X is halogen or a small anion with (ii) a free-radical co-polymerizable compound,
   (b) forming the article from the resulting polymer,
   (c) cross-linking the resulting polymer, and
   (d) complexing the resulting article with iodine.

8. A process for making a polymer comprising the steps of
   (a) polymerizing (i) a quaternary ammonium compound of the formula

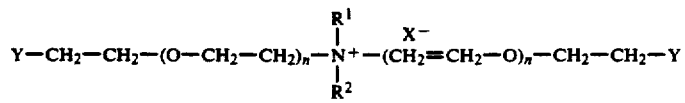

wherein —Y is —OH or —NH$_2$, R$^1$ and R$^2$ are independently alkyl or aryl, X is halogen or a small anion, and n is an integer from 0–50 with (ii) a condensation co-polymerizable compound, (b) cross-linking the resulting polymer to make an article, and (c) complexing the article with iodine.

9. The process of claim 8 wherein R$_1$ is methyl, R$_2$ is stearyl, and n is 24.

10. The process of claim 8 wherein —Y is —OH and the co-polymerizable compound is a silanol, hydrolyzable silane, or mixture thereof.

11. The process of claim 8 wherein the co-polymerizable compound is a mixture of a diisocyanate and a glycol.

12. The process of claim 8 wherein —Y is —OH and the co-polymerizable compound is a polydimethylsiloxane.

13. A composition comprising a polymer having repeating units of the formula

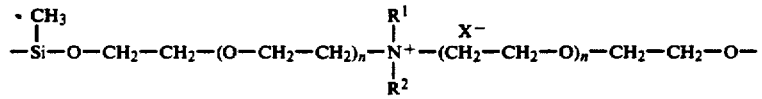

or

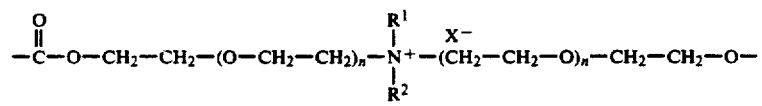

or

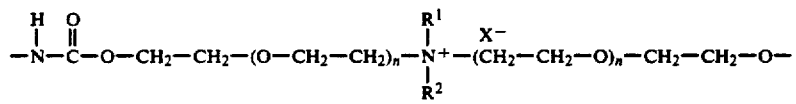

or

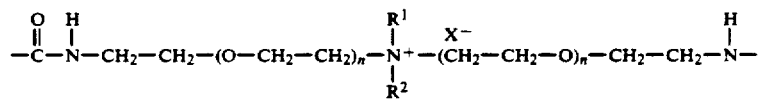

or

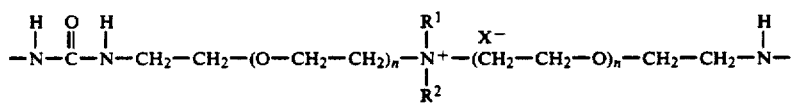

wherein R$^1$ and R$^2$ are independently alkyl or aryl, X is halogen or a small anion, and n is an integer from 1–50.

14. The composition of claim 13 having repeating units of the formula

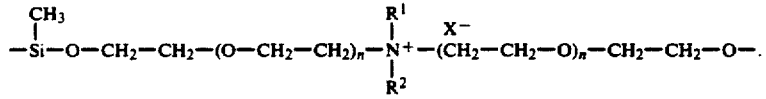

15. The composition of claim 13 having repeating units of the formula

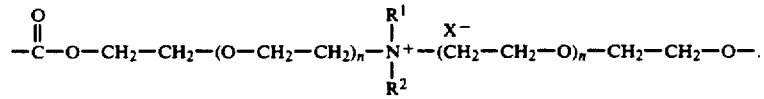

16. The composition of claim 13 having repeating units of the formula $$-\underset{\underset{H}{|}}{N}-\underset{\underset{}{\overset{O}{\|}}}{C}-O-CH_2-CH_2-(O-CH_2-CH_2)_n-\underset{\underset{R^2}{|}}{\overset{\overset{R^1}{|}}{N^+}}-(CH_2-CH_2-O)_n-CH_2-CH_2-O-\quad \overset{X^-}{}.$$

17. The composition of claim 13 having repeating units of the formula $$-\underset{}{\overset{\overset{O}{\|}}{C}}-\underset{\underset{}{\overset{H}{|}}}{N}-CH_2-CH_2-(O-CH_2-CH_2)_n-\underset{\underset{R^2}{|}}{\overset{\overset{R^1}{|}}{N^+}}-(CH_2-CH_2-O)_n-CH_2-CH_2-\underset{\underset{}{\overset{H}{|}}}{N}-\quad \overset{X^-}{}.$$

18. The composition of claim 13 having repeating units of the formula $$-\underset{\underset{}{\overset{H}{|}}}{N}-\underset{\underset{}{\overset{O}{\|}}}{C}-\underset{\underset{}{\overset{H}{|}}}{N}-CH_2-CH_2-(O-CH_2-CH_2)_n-\underset{\underset{R^2}{|}}{\overset{\overset{R^1}{|}}{N^+}}-(CH_2-CH_2-O)_n-CH_2-CH_2-\underset{\underset{}{\overset{H}{|}}}{N}-\quad \overset{X^-}{}.$$

19. An elastomeric article comprising the polymer of claim 14.
20. The article of claim 19 complexed with iodine.
21. An elastomeric article comprising the polymer of claim 15.
22. The article of claim 21 complexed with iodine.
23. An elastomeric article comprising the polymer of claim 16.
24. The article of claim 23 complexed with iodine.
25. An elastomeric article comprising the polymer of claim 17.
26. The article of claim 25 complexed with iodine.
27. An elastomeric article comprising the polymer of claim 18.
28. The article of claim 27 complexed with iodine.
29. The method of claim 7 further comprising the step of complexing the elastomeric article with iodine.

* * * * *